United States Patent [19]

Petrow

[11] Patent Number: 4,659,566
[45] Date of Patent: Apr. 21, 1987

[54] COMPOSITIONS AND METHODS FOR PERMANENTLY WAVING OR STRAIGHTENING HAIR

[76] Inventor: Henry G. Petrow, 32 Garfield Dr., Watertown, Mass. 02172

[21] Appl. No.: 642,921

[22] Filed: Aug. 21, 1984

[51] Int. Cl.$^4$ .......................... A61K 7/09; A61K 7/11; A45D 7/00
[52] U.S. Cl. ........................................ 424/71; 424/72; 132/7
[58] Field of Search ........................ 424/71, 72; 132/7

[56] References Cited

U.S. PATENT DOCUMENTS

| | | | |
|---|---|---|---|
| 2,153,762 | 4/1939 | Kritchevsky | 8/94.14 |
| 3,676,550 | 7/1972 | Auzuino | 424/71 |
| 3,824,304 | 7/1974 | Villanueva | 424/70 |
| 3,912,808 | 10/1975 | Sokol | 424/71 |
| 3,966,903 | 6/1976 | Torii et al. | 424/72 |
| 4,273,143 | 6/1981 | Klemm et al. | 424/71 |
| 4,295,985 | 10/1981 | Petrow | 252/105 |
| 4,366,827 | 1/1983 | Madrange et al. | 424/71 |

FOREIGN PATENT DOCUMENTS

| | | |
|---|---|---|
| 0037224 | 10/1981 | European Pat. Off. . |
| 57-2216 | 1/1982 | Japan .................................... 424/71 |
| 1475971 | 6/1977 | United Kingdom . |

OTHER PUBLICATIONS

Ebert, Chem. Abst. 47168p (1966), vol. 66.
Sagarin, *Cosmetics: Science and Technology*, pp. 618 and 1067 (1957).

*Primary Examiner*—Jerome D. Goldberg
*Assistant Examiner*—F. Krosnick
*Attorney, Agent, or Firm*—Pennie & Edmonds

[57] ABSTRACT

The invention relates to novel reducing compositions for reducing the disulfide bonds of keratin, comprising a regenerable reducing agent, such as an iodide salt, ferrocyanide salt, bromide salt and antimony(III) tartrate salt, capable of reducing the disulfide bonds of keratin, in combination with a consumable reducing agent, such as a salt or ester of thioglycolic acid, or a sulfite, bisulfite, hydrosulfite, metabisulfite or sulfoxylate salt, in which the consumable reducing agent is capable of regenerating the regenerable reducing agent by reducing the oxidized form of the regenerable reducing agent. Neutralizing compositions compatible with such reducing compositions, as well as methods for permanently waving or straightening hair or fur, are also encompassed by the invention.

20 Claims, No Drawings

COMPOSITIONS AND METHODS FOR PERMANENTLY WAVING OR STRAIGHTENING HAIR

TABLE OF CONTENTS

1. Field of the Invention ...
2. Background of the Invention ...
   2.1. Use of Iodine/Iodide ...
3. Summary of the Invention ...
4. Detailed Description of the Invention ...
   4.1. Reduction Systems ...
      4.1.1. Sulfite or Bisulfite System ...
      4.1.2. Ammonium Thioglycolate System ...
      4.1.3. Monoethanolammonium Thioglycolate System ...
      4.1.4. Glycerol Thioglycolate System ...
   4.2. Neutralization Systems ...
5. Examples: Preparation and Methods of Use ...
   5.1. Formulations ...
      5.1.1. Bisulfite/Iodide ...
      5.1.2. Ammonium Thioglycolate/Iodide ...
      5.1.3. Monoethanolammonium Thioglycolate/Iodide ...
      5.1.4. Glycerol Thioglycolate/Iodide ...
   5.2. Methods of Use ...
   5.3. Curling Hair Samples ...
      5.3.1. Bisulfite/Iodide Treatments ...
      5.3.2. Ammonium Thioglycolate/Iodide Treatments ...
      5.3.3. Monoethanolammonium Thioglycolate/Iodide Treatments ...
      5.3.4 Glycerol Monothioglycolate/Iodide Treatments ...
6. Effect of Iodide Systems in Controlling Hair Damage ...
7. Salon Tests on Hard-to Curl Hair ...
   7.1. Fragile Hair ...
   7.2. Oriental Hair ...
   7.3. Hard-to-Perm Caucasian Hair ...
8. Example: Straightening Hair ...
9. Claims

1. FIELD OF THE INVENTION

The present invention is directed to new and improved methods of permanently waving hair, and novel compositions of matter useful in such improved methods. The novel compositions may also be useful for altering the shape of hair by relaxing or straightening naturally or artifically waved hair.

2. BACKGROUND OF THE INVENTION

Conventional methods for permanently waving keratinous fibers, particular hair, generally consist of a two stage process. Initially the hair is shampooed, and mechanically positioned into the configuration or shape desired. Generally this is acheived by wrapping the hair around cylinders (termed "rollers") of the appropriate size to either impart a curl or wave or to straighten waved hair.

In the first stage of process, referred to as the reduction stage, the disulfide linkages (S—S) of the keratin fiber are opened (reduced to two mercaptan groups), with the aid of reducing agents, including thioglycolates, sulfites, and bisulfites, etc. Depending upon the systems used, the hair is exposed either to acidic or alkaline values of pH. Thereafter, the hair is rinsed extensively and subsequently treated with a mild oxidizing agent in a second stage operation, referred to as a neutralization stage, to form new S—S linkages and to impart the desired configuration to the hair. Generally used neutralizing agents include hydrogen peroxide and sodium bromate (Robbins, Chemical and Physical Behavior of Human Hair, Van Nostrand Reinhold Company, New York (1979)).

Conventional techniques, however, have suffered from a number of disadvantages. In particular, thiol containing compositions suffer from a persistent disagreeable sulfur odor. Other compositions suffer from the irritating odor of ammonia when utilized at alkaline values of pH. Sulfite and bisulfite systems when used for "home perms" require an extensively long period of time in contact with the hair, e.g., one hour or so, and typically produce curls of less than professional standards. Additionally, since many of the other conventional ingredients are caustic to both hair and skin, safety considerations do not allow for home use formulations as concentrated as typically used in professional salons. Consequently, such "home perm" systems are not as effective, i.e., curl is not as tight and does not last as long, as available professionally. More importantly, the conventional systems tend to damage the hair (presumably through hydrolysis of peptide and amide linkages), particularly if left in contact with the hair for an extended time. The permed hair generally becomes brittle, dry, and loses agreeable tactile quality.

2.1. USE OF IODINE/IODIDE

Conventional techniques for hair waving or straightening have not involved the use of water soluble-iodide salts as described herein according to the preferred embodiment of the present invention.

Use of a mixture of iodine/iodide for treating hair for other purposes has, however, been previously described. In particular, Kritchensky (U.S. Pat. No. 2,153,762 issued Apr. 11, 1939) described use of a mixture of iodine, potassium iodide and sodium chloride as a first step prior to a lustering operation for improving the luster and decreasing the tendency of wool or hair to curl or spot when exposed to moisture. Kritchensky stated that absorption of the iodine in the mixture was necessary for reaction with unsaturated bonds in the hair to make the hair coarse and non-curling.

U.S. Pat. No. 3,824,304, issued to Villanueva on July 16, 1974, describes use of a tincture of iodine, i.e., a mixture of iodine and sodium iodide in an alcoholic solvent, to condition hair.

3. SUMMARY OF THE INVENTION

The present invention involves novel formulations that are useful for permanently altering the shape or configuration of keratinous fibers, particularly hair, or fur. The formulations and methods of use described herein are more efficient and represent distinct improvements over conventional techniques of permanent hair or fur waving and relaxing.

According to the present invention, a heretofore unusable reducing agent ($RA_1$), that has rapid kinetics but not necessarily a useful equilibrium constant for tne cleavage of disulfide linkages in keratin, is combined with a conventionally used reducing agent ($RA_2$) that has a usefully high equilibrium constant but not necessarily rapid reaction kinetics. According to the inventor's theoretical understanding of the chemistry involved, the primary agent for cleaving the disulfide linkages is now $RA_1$, which is very rapidly and substantially completely regenerated from its oxidized form by $RA_2$, which is consumed in the process. It is to be understood, however, that successful practice of the inventions described herein does not depend on the correctness of such theoretical understanding, and that the invention shall not be limited to any particular chemical mechanism. Practice of the methods described herein and use of the formulations of the invention result in the advantages described, independent of such theoretical concerns.

In the preferred embodiment of the present invention, the regenerable reducing agent is a water-soluble iodide salt including, but not limited to: simple salts such as potassium iodide, sodium iodide, and ammonium iodide. In other embodiments, potassium ferrocyanide, sodium bromide and antimony (III) potassium tartrate may be used as the regenerable reducing agent, but they are less effective than iodides.

The combinations of the present invention are useful in improving the kinetics of the reduction stage in permanent waving and hair straightening systems. When used in systems containing sulfites or bisulfites, the improvement is such that these odorless systems can produce professional quality permanent waves, which was not possible heretofore.

The combinations of the present invention when used in thioglycolate systems have the very important and surprising benefit of significantly reducing the usual hair damage associated with waving, because:

(a) The caustic thioglycolic reducing agents can be used at lower concentrations, because of the improved kinetics.

(b) If used at conventional concentrations, such caustic agents can be left in contact with the hair for a shorter period of time, because of improved kinetics.

(c) Overprocessing is avoided because the consumable thioglycolate reducing agents are rapidly used up in the process of reducing iodine to iodide, which reaction is favored over the thioglycolate reaction with the hair.

(d) Most importantly and surprisingly, the regenerable reducing agent which is primarily responsible for the disulfide cleavages is apparently very selective for this reaction since it is innocuous at the concentrations used as far as hair damage is concerned.

In addition, because of the improved kinetics of the reactions of this invention, the gentle and slow acting monoethanolammonium thioglycolate, which has heretofore been largely limited to home waves, can now surprisingly be used in professional salon cold waves as a practical substitute for the ammonia thioglycolate system, thereby eliminating the irritating ammonia fumes associated with such systems.

4. DETAILED DESCRIPTION OF THE INVENTION

As described supra in Section 2, the conventional method for permanently waving hair fibers consists in a first reducing stage operation in which the disulfide linkages (S—S) of the keratin fiber are broken with the aid of a reducing agent. Thereafter, the hair is preferably rinsed well and subsequently treated in a second stage operation with a neutralizing agent to form new S—S linkages of the keratin to impart to the hair the desired configuration or shape.

4.1. REDUCTION SYSTEMS

According to the present invention in the first reducing stage of the two-stage process for hair treatment, a regenerable reducing agent ($RA_1$) that has rapid kinetics, but not necessarily a useful equilibrium constant for the reaction in which the disulfide linkages of keratin in hair fibers are reduced, is combined with a consumable reducing agent ($RA_2$) that has a usefully high equilibrium constant, but not necessarily rapid reaction kinetics for the keratin reduction reaction.

By "useful" as applied to the equilibrium constant is meant that if the reaction were allowed to reach equilibrium, the amount of reduced keratin present, when subsequently oxidized (neutralized), would provide an acceptable curl. In this context "useful" does not indicate that the reaction would occur within an acceptable time frame for purposes of curling or straightening hair or fur. Generally, an acceptable time frame would be less than about one hour, preferably about ten to twenty minutes. Conversely, a reaction which does not have a useful equilibrium constant would not, if allowed to reach equilibrium, provide a sufficient amount of reduced keratin to impart an acceptable curl after subsequent neutralization.

By the term "rapid reaction kinetics" is meant that the reduction reaction is fast enough to provide, within an acceptable time frame, sufficient reduced keratin which, after subsequent neutralization, would provide an acceptable curl. Again, an acceptable time frame would be about one hour, preferably ten to twenty minutes.

Based upon the inventor's proposed theoretical mechanism of this reaction, it is presumed that the oxidized form of the regenerable reducing agent ($RA_{1-ox}$) is rapidly and essentially completely reduced to $RA_1$ by the consumable reducing agent. While the consumable reducing agent apparently does some useful work of cleaving disulfide bonds, the main work surprisingly seems to be accomplished by the regenerable reducing agent, which by itself is not capable of cleaving the disulfide bonds in a detectable amount because of its very low equilibrium constant for this reaction. (In fact the reverse reaction, neutralization with iodine solution, proceeds very rapidly.) As shown in Table III (see Section 5.3.2), for example, ammonium thioglycolate systems, which on their own produce poor curls in five minutes, when combined with potassium iodide produce very good curls in the same amount of time.

Increased efficacy of formulations of the present invention is conferred by the combination of a consumable reducing agent with the regenerable reducing agent. Specifically, according to the preferred embodiment, a water-soluble iodide salt such as simple iodide salts including, but not limited to potassium iodide (KI), sodium iodide (NaI), or ammonium iodide (NH₄I), is utilized as the regenerable reducing agent. Combination of the regenerable and consumable reducing agents enhances the efficacy of compositions containing only the corresponding consumable reducing agent by permitting the reduction of disulfide linkages of the keratin to proceed at a faster rate.

Moreover, the hair is damaged less because the damaging consumable reducing agent in the combinations of the present invention: (a) can be in contact with the hair for a shorter period of time; (b) may be used in lower or more dilute concentrations; and (c) presumably is consumed rapidly by the oxidized-form of the regenerable reducing agent which reacts more selectively. Hence, the combinations of the present invention inherently protect against overprocessing of the hair because the damaging consumable reducing agent is rapidly consumed by the iodine in the process while the regenerable reducing agent, which is primarily responsible for the disulfide cleavage, is apparently very selective for this reaction since it is innocuous at the concentrations employed as far as hair damage is concerned. Other advantages of specific embodiments are indicated infra.

The chemical reactions in the first reduction stage operation of hair treatment according to the present invention may be represented by the generalized equations as follows:

$$\text{Keratin} + RA_1 \underset{k_5}{\overset{k_4}{\rightleftharpoons}} \text{Keratin-reduced} + RA_{1-ox} \quad (1)$$

wherein the equilibrium constant for the reaction is $K_1(eq)$, and $k_4$ and $k_5$ represent the forward and reverse reaction rate constants. "Keratin" represents the disulfide-bound keratin protein, and "Keratin-reduced" represents reduced protein and "$RA_{1-ox}$" represents the oxidized form of reducing agent $RA_1$.

The equilibrium constant for the reaction of equation (1) may be computed as follows:

$$K_1(eq) = \frac{[RA_{1-ox}][\text{Keratin-reduced}]}{[RA_1][\text{Keratin}]} = \frac{k_4}{k_5}. \quad (2)$$

The expression (2) above may be rewritten such that $$\frac{[\text{Keratin-reduced}]}{[\text{Keratin}]} = K_1(eq) \times \frac{[RA_1]}{[RA_{1-ox}]} \quad (3)$$

If the value of $[RA_{1-ox}]$ is made very small, i.e., by reduction by the consumable reducing agent, then the corresponding value of $$\frac{[\text{Keratin-reduced}]}{[\text{Keratin}]}$$

becomes usefully large, that is, the reaction of Equation (1) would be "driven" in favor of Keratin-reduced, and sufficient amounts of reduced keratin would be formed such that after neutralization an acceptable curl results.

The reaction of the regeneration of the regenerable reducing agent by the consumable one is represented as follows:

$$RA_{1-ox} + RA_2 \underset{k_7}{\overset{k_6}{\rightleftharpoons}} RA_1 + RA_{2-ox} \quad (4)$$

wherein $K_2(eq)$ is the equlibrium constant for the reaction and $k_6$ and $k_7$ represent the forward and reverse reaction rate constants.

The equilibrium constant for the reaction of equation (4) may be computed as follows:

$$K_2(eq) = \frac{[RA_1][RA_{2-ox}]}{[RA_{1-ox}][RA_2]} = \frac{k_6}{k_7}. \quad (5)$$

Expression (5) above may be rewritten as $$\frac{[RA_1]}{[RA_{1-ox}]} = K_2(eq) \times \frac{[RA_2]}{[RA_{2-ox}]} \quad (6)$$

Substitution of this ratio into expression (3) above gives $$\frac{[\text{Keratin-reduced}]}{[\text{Keratin}]} = K_1(eq) \times K_2(eq) \frac{[RA_2]}{[RA_{2-ox}]}. \quad (7)$$

The equation for the reaction of the consumable reducing agent with keratin is $$\text{Keratin} + RA_2 \underset{k_9}{\overset{k_8}{\rightleftharpoons}} \text{Keratin-reduced} + RA_{2-ox} \quad (8)$$

wherein the equilibrium constant for the reactions is $K_3(eq)$ and $k_8$ and $k_9$ represent the forward and reverse reaction rate constants.

The equilibrium constant for the reaction of Equation (8) may be computed as follows:

$$K_3(eq) = \frac{[\text{Keratin-reduced}][RA_{2-ox}]}{[\text{Keratin}][RA_2]} \quad (9)$$

Equation (9) may be rewritten as $$\frac{[\text{Keratin-reduced}]}{[\text{Keratin}]} = K_3(eq) \frac{[RA_2]}{[RA_{2-ox}]}. \quad (10)$$

Comparing Equations (7) and (10), it can be seen that

(11) $K_1(eq) \times K_2(eq) = K_3(eq)$

In addition to Equation (11), the constraints upon the choice of particular compounds for $RA_1$ and $RA_2$ include the following:

(i) $K_3(eq) > K_1(eq)$

As described above, $RA_2$ has a useful equilibrium constant for the reduction of disulfide bonds, but the reaction may not proceed rapidly enough. On the other hand, no matter how long one observes the reaction of the reduction of Keratin by $RA_1$, it will not proceed to an appreciable extent since the equilibrium constant is so small. From effective conventional compositions containing a single reducing agent, such as thioglycolate, the equilibrium constant for reduction of Keratin may be estimated to be in the range of about $10^{-1}$ to 10. Thioglycolate for example, has an equilibrium constant of approximately 1. Since $RA_1$ alone does not result in appreciable reduction of keratin, i.e., $K_1(eq)$ is very small, for example, $10^{-10}$ to $10^{-20}$, $K_3$eq is greater than $K_1(eq)$.

(ii) $k_6 > k_5$

In order to "drive" the reduction of Keratin by $RA_1$ in favor of producing Keratin-reduced, the $[RA_{1-ox}]$ must be reduced by the action of $RA_2$ in accordance with Equation (4). Thus, $k_6$ must be very large relative to $k_5$.

(iii) $K_2(eq) > K_1(eq)$

In accordance with Equation (11), when $K_3(eq) > K_1(eq)$ [(i) above], then $K_2(eq) > K_1(eq)$. Based upon the relationships among the three equilibrium constants, $K_2(eq)$ would be expected to be very large, for example, in the range of to $10^{10}$ to $10^{20}$.

(iv) $k_6 > k_8$

The qualitative description for this constraint is that the rate of regeneration of $RA_1$ by $RA_2$ is greater than the rate of reduction of Keratin by $RA_2$.

(v) $k_4 > k_8$

Both of constraints (iv) and (v) must be true in order for one to observe an effect upon addition of $RA_1$. If $k_8$ were larger than $k_4$ and $k_6$, the reaction of $k_8$ would be the fastest reaction and addition of $RA_1$ would have no effect.

Since the "concentration" of disulfide bonds of keratin can not be accurately estimated, and since such a figure would necessarily vary depending upon hair type and from individual to individual, numbers for the equilibrium constants $K_1(eq)$ and $K_3(eq)$ can only be approximated.

The relationship of Equation (11) among the three equilibrium constants always holds by chemical law, and the critical factors are the kinetics of $K_1(eq)$ and $K_2(eq)$ relative to those of $K_3(eq)$. What is truly surprising is that the reaction of $K_1(eq)$ with its minute equilibrium constant should have a $k_4$ that is greater than $k_8$.

According to the preferred embodiment of the present invention, the regenerable reducing agent ($RA_1$) is a water-soluble iodide salt such as simple iodide salts including potassium iodide (KI), sodium iodide (NaI), or ammonium iodide ($NH_4I$). When KI is utilized as $RA_1$, the kinetics of expression (1) above are excellent in that the reaction proceeds rapidly and iodide diffuses readily through the hair.

Other salts which may be used as regenerable reducing agents include, but are not limited to: ferrocyanides, bromides, and antimony (III) tartrates. In comparison with soluble iodide salts, the latter salts are far less effective being fair, weak and weak, respectively, relative to iodide in their enhancing effects on hair waving compositions. Although potassium thiocyanate (KSCN) is close in redox and electrolytic properties to KI, KSCN is not effective at all in the compositions of the present invention. Similarly, potassium chloride is not effective at all. Other common salts which also are not effective include various sulfates and nitrates.

To evaluate quantitatively the contribution of KI to increasing the perming rate and degree of curl formation, the following experiments were performed. Exactly 1 gm samples of untreated brown hair were shampooed, blotted dry, and wrapped on rollers. A total of 10 samples were prepared in this way. Five of them were impregnated with exactly 1 ml each of 1.0 M monoethanolammonium thioglycolate adjusted to pH 9.3 with monoethanolamine. The remaining glycolate solution was made 0.3 M in KI and the five remaining hair samples impregnated with exactly 1 ml each of this solution. All 10 samples were allowed to react at ambient temperature (approx. 75° F.) for 5 minutes and then quenched and allowed to soak in 600 ml of water. Each sample was well agitated to thoroughly rinse out unreacted agents. The amount of unreacted thioglycolate was determined by titration with standard iodine solution. For the five samples containing no KI, the average thioglycolate consumption was 36%. For the samples containing KI, the average consumption was 54%. An additional 2 samples were impregnated with 1.0 M thioglycolate (pH 9.3) solution, one with and one without KI, and allowed to set for 30 minutes. The thioglycolate consumption was 60% with KI and 63% without KI.

All the samples were neutralized with 10% $NaBrO_3$ solution for 5 minutes, unrolled, rinsed, and allowed to air dry.

All the samples containing KI yielded professional quality curl formation with no discernible hair damage. The 5 samples treated without KI yielded curls of poor quality. The sixth sample without KI which was allowed to react for 30 minutes yielded a well-formed curl, but the hair showed discernible damage as evidenced by rough, stiff tactile qualities.

In these experiments, the addition of KI increased the rate and quality of curl formation and eliminated hair damage. One can reasonably infer from these experiments that in the presence of KI and the thioglycolate compound, the preferred reaction is the splitting of the disulfide bonds by the iodide-iodine regeneration reaction. Thus, the thioglycolate would be consummed to regenerate iodide.

This was confirmed in similar experiments in which data was obtained at various reaction times from 1.5 to 8 minutes. Analysis of these data establish that the reaction rate in the presence of 0.3 M KI is 3 times as fast as is found with thioglycolate alone. That is, in the thioglycolate-iodide system 75% of the disulfide bond splitting is a result of the iodide interaction.

According to the present invention, the compounds listed in Table I (which should not be considered an exhaustive list) may be utilized as consumable reducing agents. As illustrated in Table I, a number of these substances may be used as reducing agents in the absence of a regenerable reducing agent. Enhanced results are achieved when each of the listed compounds is combined with a regenerable reducing agent as described supra. In all the systems listed in Table I there is a substantial improvement when KI is used due to the improvement in kinetics.

TABLE I

| COMPOUNDS PROVIDING CONSUMABLE REDUCING AGENTS | |
|---|---|
| Compound | Activity Without Regenerable Reducing Agent |
| Ammonium thioglycolate | good |
| Glycerol thioglycolate | good (+ heat)[a] |
| Monoethanolammonium thioglycolate | medium |
| Sodium sulfite | fair |
| Sodium bisulfite | fair + |
| Sodium hydrosulfite | fair |
| Ammonium sulfite | fair |
| Ammonium bisulfite | fair |
| Potassium sulfite | fair |
| Potassium bisulfite | fair + |
| Sodium formaldehyde bisulfite | poor − |
| Sodium formaldehyde sulfoxylate | poor − |

[a]Indicates that heat activation is required.

4.1.1. SULFITE OR BISULFITE SYSTEM

In one embodiment of the present invention, either the sulfite ($SO_3^=$) or bisulfite ($HSO_3^-$) ion is utilized as the consumable reducing agent ($RA_2$). The useful concentration range of $RA_2$ is about 0.3–2.0 M, the preferable concentration being about 0.7 to 1.5 M. Preferred cations include: potassium ($K^+$), ammonium ($NH_4^+$), sodium ($Na^+$) and a mixture of $Na^+$ and $NH_4^+$. The preferred regenerable reducing agent ($RA_1$) is the soluble iodide ion. The useful concentration range for iodide is about 0.05–1.0 M, preferably about 0.15–0.4 M. Any of the cations as used for the $RA_2$ may be utilized for the $RA_1$. The useful pH range for the combination of reducing agents is about 4-10, preferably about 6-7.5.

When either $SO_3^=$ or $HSO_3^-$ is used as the $RA_2$, the composition is useful particularly when employing a heat-activated method of application. The heat may be supplied by use of a dryer with a cap or by use of body heat contained with a cap. In the latter instance, the composition is allowed to remain on the hair for a somewhat longer period of time, e.g., about 15-30 minutes, compared to about 10-20 minutes when a dryer is used. A permanent wave that meets professional standards is achieved.

In practice, when $K^+$ is utilized as the cation, the composition of the present invention is substantially odorless at all values of pH in the preferred range, and has excellent diffusional properties so that the active ingredients are rapidly delivered to the S—S linkage sites of the hair. Thus, this embodiment of the present invention offers a number of distinct additional advantages over conventional techniques, particularly: (a) lack of persistent unpleasant odor; and (b) more rapid reaction rate which reduces processing time and (c) most importantly and for the first time, enhanced curl formation that is equivalent to that achieved by thioglycolic acid systems.

In practice, when either $NH_4^+$ or a mixture of $NH_4^+$ and another cation such as $Na^+$ is utilized as the cation, the disagreeable odor of sulfur dioxide is detected when used below the preferred range of pH, and the odor of ammonia is detected when used above the preferred range of pH.

4.1.2. AMMONIUM THIOGLYCOLATE SYSTEM

In another embodiment of the present invention, the thioglycolate ($HSCH_2COO^-$) ion is utilized as the consumable reducing agent ($RA_2$). The useful concentration range is about 0.4-1.2 M, preferably about 0.5-1.0 M. The preferred cation is $NH_4^+$. The preferred regenerable reducing agent ($RA_1$) is iodide. The useful concentration range of iodide is about 0.05-1.0 M, preferably about 0.15-0.4 M. The same cation as used for the $RA_1$ may be utilized for the $RA_2$. The useful pH range for this combination of reducing agents is about 9.0-9.5. The composition has a distinct odor of ammonia at such pH values. Also present is the characteristic odor of sulfur of thioglycolate compositions. This thioglycolate odor persists for a substantial period of time post-treatment and is particularly noticeable and objectionable when the hair is damp.

When ammonium thioglycolate is used as the $RA_2$, and the pH adjusted to from 9.0-9.5 with ammonia, this composition is useful particularly when employed as a "cold wave" system. Thus, the composition is generally applied to and reacted with the hair at ambient or room temperature.

When iodide is used as the $RA_1$, the composition is allowed to remain on the hair for about 3-10 minutes. This represents a distinct advantage over conventional ammonium thioglycolate systems which require contact with normal hair for about 10-30 minutes.

The composition of this embodiment represents distinct improvements over conventional ammonium thioglycolate systems because the thioglycolate (a) is in contact with the hair for a shorter time period; and/or (b) can be used at lower concentration (see Table III, Section 5.3.2). Moreover, the present composition offers inherent protection against overprocessing the hair because the damaging ammonium thioglycolate is so rapidly consumed in the course of regenerating the iodide and cleaving disulfide bonds. This is particularly important under all conditions of use contemplated for the composition, since the major negative side effect of permanent waving is hair damage. The present invention also guards against aggravated hair damage resulting from inexperience, carelessness, and too concentrated solutions.

4.1.3. MONOETHANOLAMMONIUM THIOGLYCOLATE SYSTEM

In another embodiment of the present invention the thioglycolate ion ($HSCH_2COO^-$) is also utilized as the consumable reducing agent ($RA_2$). The useful concentration range of $HSCH_2COO^-$ is about 0.4-1.2 M, preferably about 0.7-1.2 M. The cation for $RA_2$ in this embodiment is the monoethanolammonium ion. The preferred regenerable reducing agent ($RA_1$) is iodide. The useful concentration range for iodide is about 0.05-1.0 M, preferably 0.15-0.4 M. Useful cations for the $RA_1$ include $Na^+$ and $K^+$. The preferred composition should be adjusted to pH about 9.0-9.5 with monoethanolamine.

In practice, the monoethanolammonium thioglycolate composition of this embodiment is particularly useful when applied as a "cold wave", i.e., at ambient or room temperature. When thus used, the composition can be used to achieve a permanent wave that meets professional standards and the objectionable, irritating fumes of ammonia are eliminated. Heretofore, monoethanolammonium thioglycolate compositions have been largely restricted to home perms.

4.1.4. GLYCEROL THIOGLYCOLATE SYSTEM

In still another embodiment of the present invention, the glycerine ester of thioglycolic acid, glycerol monothioglycolate, is utilized as the $RA_2$. The preferred range for this $RA_2$ is about 0.6-1.5 M. The preferred $RA_1$ is the iodide ion which is utilized in the form of soluble alkaline salts such as $Na^+$, K, and $NH_4^+$ and the like. In this system, the $RA_1$ and $RA_2$ must be mixed together just prior to use because glycerol thioglycolate hydrolyzes in water. The preferred pH range is about 6.7-7.3, and aqueous ammonia is the preferred base used to adjust the value of pH.

In practice, the glycerol monothioglycolate composition of this embodiment may be advantageously be applied either as a "cold wave" or as a heat-activated formulation. Heretofore, this material was useful primarily only when heat activated.

4.2. NEUTRALIZATION SYSTEMS

As explained previously, a second stage operation comprising application of a neutralizing agent is necessary to form new S—S linkages of the keratin fibers in order to maintain the hair in the desired curled or straight configuration.

According to the present invention in the second stage of operation, the preferred neutralizing agent is aqueous sodium bromate ($NaBrO_3$).

In practice, the neutralization stage of operation is performed as follows: after treatment of the hair with a reducing composition, the hair is rinsed thoroughly to remove the reducing agents, blotted, and a neutralizing agent applied to the hair which is mechanically maintained in the desired configuration. After about five minutes, the hair is briefly rinsed, released, i.e., unwrapped from rollers, rinsed again, and allowed to dry.

When the hair has been treated with an alkaline composition, it may initially be rinsed for about three minutes. When the hair has been treated with an acid composition, the hair is less porous and should be rinsed initially for at least five minutes.

As a practical consideration, when an acid composition at a pH less than about 6.5–6.7 containing iodide as the regenerable reducing agent has been used, it is important to rinse thoroughly. For example, if a sulfite composition described supra in Section 4.1.1 is used, a small amount of iodine may be formed by oxidation of any residual iodide present. The presence of such iodine may be detected as a slight yellow color on any end papers used to wrap the hair. At pH about 6.7 or higher, such reaction does not occur with bromates. With the commonly used acidified hydrogen peroxide ($H_2O_2$) neutralizers, iodine formation occurs.

According to the present invention, other agents that can be utilized as neutralizing agents for the second stage when iodide is used as the regenerable reducing agent include: sodium or potassium antimony (V) tartrate, and a composition comprising a solution of $H_2O_2$ to which is introduced at the time of use a "protective" reducing agent which reacts only slowly with $H_2O_2$ but rapidly with iodine. The protective reducing agent acts to reduce any iodine formed to iodide. Such reducing agents include ascorbic acid and carbazide. In practice, a solution of less than 3% $H_2O_2$ containing such reducing agent is used. In general, about 1–5% ascorbic acid or carbazide is sufficient. The useful pH range is about 1.5–3.8, preferably about 1.5–2.5. The preferred pH is generally achieved by the addition of phosphoric acid.

The neutralizing compositions of the present invention can also contain a thickening agent such as carboxymethyl cellulose, conditioning agents such as mineral oil, lanolin, or other suitable quaternary ammonium salts. Further the composition can also contain certain other conventional cosmetic adjuvants such as perfume, dyes, stabilizers, preservatives and surfactants.

The following examples are given for the purpose of illustration and not by way of limitation on the scope of the invention.

5. EXAMPLES: PREPARATION AND METHODS OF USE

5.1. FORMULATIONS

Examples presented below demonstrate formulations for reducing compositions that were prepared as described supra in Section 4. The active ingredient listed represents the initial starting ingredient used to prepare the formulation. In each case, sodium laureth sulfate (Henkel Corp.) (0.5% by weight) was added to the composition as a wetting agent or surfactant. There was, however, nothing to indicate that such surfactant is essential to the activity of the compositions.

5.1.1. BISULFITE/IODIDE

Representative bisulfite/iodide reduction systems include:

| Active Ingredient | Concentration (Molarity) |
| --- | --- |
| Sodium bisulfite | 1.0 |
| Potassium Iodide[a] | 0.3 |
| Ammonia (aqueous)[b] | |

[a]USP Grade (E & F King)
[b]Added as reagent grade (28%) (Fischer Scientific) to adjust pH to 6.8.

5.1.2. AMMONIUM THIOGLYCOLATE/IODIDE

Representative thioglycolate/iodide reduction systems include:

| Active Ingredient | Concentration (Molarity) |
| --- | --- |
| Ammonium thioglycolate[a] | 1.1 |
| Potassium Iodide | 0.3 |
| Ammonia (aqueous)[b] | |

[a]Added as cosmetic grade, i.e., 60% contained thioglycolic acid (Evans Chemical).
[b]Added as reagent grade (28%) (Fischer Scientific) to adjust pH to 9.3.

5.1.3. MONOETHANOLAMMONIUM THIOGLYCOLATE/IODIDE

Representative monoethanolammonium thioglycolate/iodide reduction systems include:

| Active Ingredient | Concentration (Molarity) |
| --- | --- |
| Monoethanolammonium thioglycolate[a] | 1.1 |
| Potassium Iodide | 0.3 |
| Monoethanolamine[b] | |

[a]Added as 39.2% contained thioglycolic acid (Evans Chemical).
[b]Reagent grade (Fischer Scientific) added to adjust pH to 9.3.

5.1.4. GLYCEROL THIOGLYCOLATE/IODIDE

Representative glycerolthioglycolate/iodide reduction systems include:

| Active Ingredient | Concentration (Molarity) |
| --- | --- |
| Glycerol Monothioglycolate[a] | 1.1 |
| Potassium Iodide | 0.3 |
| Ammonia (aqueous)[b] | |

[a]Added as cosmetic grade, i.e., 80% glycerol monothioglycolate in glycerine (Evans Chemical).
[b]Added as reagent grade (28%) (Fischer Scientific) to adjust pH to 6.8.

5.2. METHODS OF USE

The following experiments demonstrate methods of application and results obtained when using the compositions according to the present invention.

In each of the experiments 0.5 gm of Caucasian hair (about 7 inches in length) (DeMeo Brothers, New York, NY) was secured at one end with a plastic tab, shampooed using Purifying Shampoo ™ (Eljenn International Corp., Newton, MA), rinsed with water, blotted and wrapped tightly, using end papers, around rollers (about 0.5 inch diameter). The appropriate reducing composition was applied, allowed to react under conditions of time and temperature as specified, and the hair was rinsed in running water for one minute.

Ambient or room temperature was about 75° F. When experiments were performed at room temperature, the hair samples were not enclosed. When experiments were performed at higher temperatures, the hair samples were enclosed in a plastic bag which was then warmed to the desired temperature using a salon-type hair dryer.

In all cases, the neutralizing composition comprised a commercially available aqueous solution of sodium bromate (about 10%) at a pH of about 7.5 (AmeriBrom Co.).

After the hair was rinsed, the sample was blotted, the neutralizing composition applied and allowed to react with the hair for about 5 minutes. The hair was then rinsed briefly, unwrapped and rinsed well in running water. The unwrapped hair was then blotted and allowed to air dry.

The "shape", "strength" and "springiness" of tne curl achieved was then evaluated. The "shape" of the curl refers to the waved configuration perceptible in the hair sample. The "strength" of the curl refers to persistence of the curl following a single shampooing 48 hours post-treatment. The "springiness" of the curl refers to the liveliness with which a stretched curl springs back when released.

Each of the three parameters, shape, strength and springiness was evaluated post-treatment. Such evaluation is necessarily subjective. In order to afford some objectivity to the evaluation, however, the results obtained were rated and assigned a value from 0–10 according to the following scale:

| Curl Rating | Value of Curl |
| --- | --- |
| Poor | 0–2 |
| Fair | 3–4 |
| Good | 5–6 |
| Very Good | 7–8 |
| Excellent | 9–10 |

It should be noted that only curl ratings of about 8 to 10 meet cosmetically acceptable standards for professional permanent waves.

5.3. CURLING HAIR SAMPLES

5.3.1. BISULFITE/IODIDE TREATMENTS

Tables IIA and IIB present results obtained when hair samples were treated with a bisulfite/iodide reducing composition. Because the conventional bisulfite system is generally applied to human hair and then covered with a plastic cap, experiments tabulated in Table IIA were conducted at about 88° F., the approximate temperature of hair on the human head when moistened and covered with a plastic cap such as generally used for "home" permanent wave systems. In all cases the hair sample was allowed to react with the reducing compositions for 20 minutes (Table IIA)

TABLE II
APPLICATION OF BISULFITE/IODIDE

A. Temperature fixed at 88° F.
Processing time 20 minutes
Hair type: Brown

| Sodium Bisulfite (Molarity) | Potassium Iodide (Molarity) | Final pH[a] | Base | Curl Rating | Value of Curl |
| --- | --- | --- | --- | --- | --- |
| 0.7 | 0 | 6.8 | NH$_3$ | Fair | 3 |
| 0.7 | 0 | 10.1 | NH$_3$ | Poor | 2 |
| 0.7 | 0 | 6.8 | MEA[a] | Poor | 2 |
| 0.7 | 0 | 10.1 | MEA[a] | Very Poor | 1 |
| 0.7 | 0.3 | 10.1 | MEA[a] | Fair | 4 |
| 0.7 | 0.3 | 6.8 | NH$_3$ | Good | 6 |
| 1.0 | 0.3 | 6.8 | NH$_3$ | Very Good | 7 |
| 1.3 | 0.3 | 6.8 | NH$_3$ | Very Good | 7 |
| 2.0 | 0.3 | 6.8 | NH$_3$ | Good | 6 |
| 1.0 | 0.05 | 6.8 | NH$_3$ | Fair | 3+ |
| 1.0 | 0.15 | 6.8 | NH$_3$ | Fair | 4 |
| 1.0 | 0.30 | 6.8 | NH$_3$ | Good | 5+ |
| 1.0 | 0.45 | 6.8 | NH$_3$ | Good | 6 |
| 1.0 | 0.85 | 6.8 | NH$_3$ | Good | 6+ |
| 1.0 | 0.3 | 5.0 | NH$_3$ | Good | 6 |
| 1.0 | 0.3 | 6.0 | NH$_3$ | Very Good | 7 |
| 1.0 | 0.3 | 6.5 | NH$_3$ | Very Good | 7 |
| 1.0 | 0.3 | 7.0 | NH$_3$ | Good | 6+ |
| 1.0 | 0.3 | 8.0 | NH$_3$ | Good | 5 |
| 1.0 | 0.3 | 9.0 | NH$_3$ | Fair | 4 |

B. Temperature and Reaction Time Varied
Hair type: Brown

| Sodium Bisulfite (Molar) | Potassium Iodide (Molar) | Final pH | Base | Temp (°F.) | Time (Min) | Curl Rating | Value of Curl |
| --- | --- | --- | --- | --- | --- | --- | --- |
| 1.0 | 0.3 | 6.8 | NH$_3$ | 75 | 30 | Good | 5 |
| 1.0 | 0.3 | 6.8 | NH$_3$ | 88 | 30 | Very Good | 8 |
| 1.0 | 0.3 | 6.8 | NH$_3$ | 98 | 20 | Very Good | 7 |
| 1.0 | 0.3 | 6.8 | NH$_3$ | 105 | 15 | Excellent | 9 |
| 1.0 | 0.3 | 6.8 | NH$_3$ | 115 | 15 | Excellent | 10 |

[a]Monoethanolamine used to adjust pH

As previously explained, the curl or wave achieved was evaluated and rated according to a scale of 0–10. For example, as illustrated in Table IIB, an excellent curl rating a curl value of 10 was obtained using 1.0 M sodium bisulfite with 0.3 M potassium iodide at pH 6.8 for 15 minutes at 115° F. The hair sample was reduced in length about 2.5 inches, exhibiting a pronounced springy curl. After a single shampooing, the curl persisted, with the hair increasing in length at most 0.25 inch.

As demonstrated in Table IIA, the curl obtained was improved when the pH of the bisulfite system was reduced from that conventionally used (e.g., Rave[R] pH 10.1) to pH 6.8. Further, addition of the regenerable reducing agent, potassium iodide further improved results. For example, a curl rating a curl value or 1 was obtained using 0.7 M sodium bisulfite with no potassium iodide at pH of 10.1. The wave was barely perceptible. Reduction in length of the hair sample was 0.25 inch. When 0.3 M potassium iodide was added, a curl rating a value of 4 was obtained. The hair had a demonstrable wave. Reduction in length of the hair was about 1.25 inch, which reduction persisted through a single shampooing.

Increase of sodium bisulfite concentration from 0.7 M about 1.0 M, improved the rating of curl obtained. Further increase of sodium bisulfite concentration, however, to 2.0 M was no more effective than about 1.3 M.

The effect of varying the concentration of potassium iodide from 0.05 M to 0.85 M is also demonstrated (Table IIA). Above about 0.3 M potassium iodide did not improve the curl rating substantially.

The effect of varying pH on the bisulfite system is also demonstrated. As shown in Table IIA, reduction of the pH to about 5.0, did not significantly affect the curl value obtained. As the pH falls below about 6.8, however, an odor of sulfur dioxide becomes apparent. At pH about 6.8, the odor detection is minimal. Above pH 7.0, the odor of ammonia becomes apparent. Moreover, at pH greater than 9.0, the value of the curl deteriorates.

Table IIB illustrates the effect of temperature and time upon the curl obtained. As noted previously, the bisulfite system is preferably used as a heat-activated system. Cosmetically acceptable waves were obtained when the 1.0 M sodium bisulfite with 0.3 M potassium iodide was used at 88° F. for about 30 minutes or when used at elevated temperatures for about 15 minutes. Such temperatures are easily achieved using a salon-type hair dryer. A respectable wave was obtained using the same system at ambient or room temperature (about 75° F.) for 30 minutes.

In summary, the bisulfite/iodide composition can be used either as a "home" perm, i.e., either at ambient temperature or with a plastic cap over the hair (about 88° F.), or as a professionally applied "salon-type" perm using a hair dryer. Under both kinds of conditions a cosmetically acceptable wave is achieved. Further, when the pH of the composition is adjusted to about 6.8–7.2, the composition is substantially odorless in the absence of added fragrance. When the pH is lower than this range, the odor of sulfur dioxide develops, and when the pH is above this range the odor of ammonia develops. Hair treated with compositions either above or below the preferred pH range, acquires the odor of the composition as well as the odor associated with the breaking of disulfide bonds. These odors, however, disappear following the neutralization stage and do not reappear when the hair is dampened.

5.3.2. AMMONIUM THIOGLYCOLATE/IODIDE TREATMENTS

Table III illustrates results obtained when hair samples were treated with the ammonium thioglycolate/iodide system. These experiments were conducted at room temperature (about 75° F.).

TABLE III
APPLICATION OF THIOGLYCOLATE/IODIDE
Hair type: Brown

| Ammonium-thioglycolate (Molarity) | Potassium Iodide (Molarity) | Final pH[a] | Time (Min.) | Curl Rating | Value of Curl |
|---|---|---|---|---|---|
| 1.1 | 0.0 | 9.3 | 5 | Poor | 2 |
| 1.1 | 0.0 | 9.3 | 20 | Very Good | 8 |
| 1.1 | 0.3 | 9.3 | 5 | Very Good | 7 |
| 1.1 | 0.3 | 9.3 | 10 | Excellent | 10 |
| 1.1 | 0.3 | 9.3 | 20 | Excellent | 10 |
| 0.5 | 0.3 | 9.3 | 20 | Very Good | 7 |

[a]Used aqueous solution of ammonia to adjust the value of pH.

As demonstrated, a cosmetically acceptable curl could be achieved using about 0.7–1.1 M ammonium thioglycolate with 0.3 M potassium iodide for about 5–20 minutes. When no potassium iodide was added to the composition, an acceptable curl could be achieved only when the composition was reacted with hair for about 20 minutes.

The thioglycolate/iodide composition when used at pH about 9.3 has an irritating odor of ammonia plus the characteristic sulfur odor of thioglycolate and its decomposition products. Following neutralization and rinsing, the odor of ammonia disappears from the hair. The thioglycolate odor persists and is especially noticeable when the hair is dampened.

5.3.3. MONOETHANOLAMMONIUM THIOGLYCOLATE/IODIDE TREATMENTS

Table IV illustrates the improvement of curl achieved by the addition of 0.3 M potassium iodide to 1.1 M monoethanolammonium thioglycolate composition. In the presence of potassium iodide, a cosmetically acceptable curl was achieved at room temperature (about 75° F.).

TABLE IV
APPLICATION OF MONOETHANOLAMMONIUM THIOGLYCOLATE/IODIDE
Hair Type: brown

| Monoethanol-ammonium thioglycolate (Molarity) | Potassium Iodide (Molarity) | Final pH[a] | Time (Min.) | Curl Rating | Value of Curl |
|---|---|---|---|---|---|
| 1.1 | 0.0 | 9.3 | 20 | Good | 6 |
| 1.1 | 0.3 | 9.3 | 20 | Excellent | 9 |

[a]Used monoethanolamine to adjust pH to 9.3.

The monoethanolammonium thioglycolate composition possesses all the unpleasant persistent odor of thioglycolate and its decomposition products. No odor of ammonia is detectable.

5.3.4. GLYCEROL MONOTHIOGLYCOLATE/IODIDE TREATMENTS

Table V illustrates results obtained using the glycerol monothioglycolate/iodide system. In the absence of potassium iodide, cosmetically acceptable curl could be achieved only when the composition was reacted with hair at about 115° F. for about 20 minutes. With 0.3 M potassium iodide, an acceptable curl was aschieved at both ambient and elevated temperatures.

The glycerol monothioglycolate/iodide composition has no ammonia odor, but does possess the unpleasant persistent odor associated with thioglycolate.

TABLE V
APPLICATION OF GLYCEROL MONOTHIOGLYCOLATE/IODIDE
Treatment time: 20 minutes
Hair type: Brown

| Glycerol mono-thioglycolate (Molarity) | Potassium Iodide (Molarity) | Final pH[a] | Temp (°F.) | Curl Rating | Value of Curl |
|---|---|---|---|---|---|
| 1.1 | 0.0 | 6.8 | 75 | Fair | 4 |
| 1.1 | 0.0 | 6.8 | 105 | Good | 5 |
| 1.1 | 0.0 | 6.8 | 115 | Very Good | 8 |
| 1.1 | 0.3 | 6.8 | 75 | Very Good | 8+ |
| 0.9 | 0.3 | 6.8 | 105 | Excellent | 10 |
| 0.9 | 0.3 | 6.8 | 115 | Excellent | 10 |

[a]Used aqueous solution of ammonia to adjust the value of pH.

6. EFFECT OF IODIDE SYSTEMS IN CONTROLLING HAIR DAMAGE

Because conventional systems often leave the hair in a dry, brittle, fragile condition, the extent of damage to the treated hair was also evaluated. In these experiments, particularly harsh treatment conditions were employed, including the use of blonde hair which is more susceptible to damage, in order to demonstrate the surprising differences using the iodide system.

For example, a bisulfite/iodide composition was formulated as follows: 2.0 M sodium bisulfite, 0.3 M potassium iodide, adjusted to pH 6.8 using an aqueous solution of ammonia. A sample of hair was treated as described supra with the bisulfite/iodide composition for 30 minutes at 115° F. A control sample was treated identically except no iodide was added. After neutralization and shampooing, very little observable damage to the test hair was apparent, and cosmetically acceptable curl was achieved. With the control, a poor curl was obtained, and the hair had a dry, frizzy, limp appearance.

A thioglycolate/iodide composition was formulated as follows: 1.1 M ammonium thioglycolate was combined with 0.3 M potassium iodide, adjusted to pH 9.3 using ammonia. A sample of hair was treated as described supra with the thioglycolate/iodide composition for 25 minutes at ambient temperature (about 75° F.). A control sample of hair was similarly treated except that no potassium iodide was added to the control composition. After neutralization and shampooing, there was very little observable damage apparent in the hair treated with the composition containing potassium iodide. There was, however, noticeable damage to the hair treated with the composition with no potassium iodide. The latter hair sample appeared dry, brittle, and frizzy.

When the concentration of ammonium thioglycolate was reduced to 0.7 M, there was very little observable damage to hair samples treated with compositions with or without potassium iodide. The curl achieved, however, when potassium iodide was not present in the composition did not meet professional standards.

A monoethanolammonium thioglycolate/iodide composition was formulated as follows: 1.1 M monoethanolammonium thioglycolate, 0.3 M potassium iodide, adjusted to pH 9.3 using monoethanolamine. A sample of hair was treated with the monoethanolammonium thioglycolate/iodide composition for 25 minutes at ambient temperature (about 75° F.). A control sample of hair was similarly treated except that no potassium iodide was added to the composition. Very little damage was noted in the test sample. However, the control sample showed demonstrable damage and had an inferior curl.

A glycerol monothioglycolate/iodide composition was formulated as follows: 1.2 M glycerol monothioglycolate, 0.3 M potassium iodide, adjusted to pH 6.8 using an aqueous ammonia solution. A sample of hair was treated as described supra with the glycerol monothioglycolate composition for 30 minutes at 115° F. A control sample of hair was similarly treated except that no potassium iodide was added to the control composition. After neutralization and shampooing, very little damage was apparent in the test sample. The control sample, however, had a noticeably "rougher" tactile quality. Both samples had very good curls.

7. SALON TESTS ON HARD-TO-CURL HAIR

In the following examples, a composition prepared according to the methods of the instant invention, was applied in situ by experienced beauticians under normal beauty-salon conditions. The remarks with respect to hair damage, curliness, texture and tactile quality of the hair represent the candid reactions and opinion of experienced beauticians.

7.1. FRAGILE HAIR

Hair that has been bleached, tinted, or treated to change or lighten its natural color tends to become dry, fragile, and difficult to treat with conventional permanent waving systems.

An odorless composition for the reduction stage, was prepared as described in Section 5.1.1, as follows:

| Active Ingredient | Concentration (Molarity) |
| --- | --- |
| Sodium bisulfite | 1.0 |
| Potassium iodide | 0.3 |
| Monoethanolamine[a] | |

[a]Used to adjust pH to 6.8.

Hair that had previously been tinted and whose ends were "frosted" was shampooed, rinsed and wound around rollers to give the hair the desired curled configuration. The composition was formulated as a lotion and applied in situ to the hair using a heat-activated method of application. Heat was supplied by use of a standard salon-type hair dryer at the "Normal" setting for 18 minutes. The hair was then rinsed thoroughly, blotted, and a neutralizing composition comprising about 2% $H_2O_2$ adjusted to the pH of about 2.0 using phosphoric acid was then applied. In the absence of the preferred bromate neutralizing agent described in section 4.2, there was noticeable iodine formation. This iodine easily was rinsed out and did not persist.

The permed hair had a cosmetically acceptable, wavy curl, but did not feel like "permed" hair either to the recipient, a licensed beautician herself, or to the operator. There was no apparent additional damage to the already fragile hair. Loss of curl two weeks post-treatment was less than normal, according to the recipient.

7.2. ORIENTAL HAIR

In general it is more difficult to impart a permanent wave or curl to the hair of members of Oriental or Asian races.

An odorless composition for stage one was prepared as follows:

| Ingredient | Concentration (Molarity) |
| --- | --- |
| Sodium bisulfite | 1.0 |
| Potassium iodide | 0.3 |
| Ammonia (aqueous)[a] | |

[a]Used to adjust pH to 6.9

Hair of a female Oriental was shampooed, rinsed and wound around rollers. The composition was formulated as a lotion and applied in situ to the hair using a heatactivated method of application. Heat was supplied by use of a standard salon-type hair dryer at the "High" setting for 15 minutes. The hair was then rinsed thoroughly, blotted and a peroxide neutralizing composition as described in Section 4.2 supra was then applied.

The treated hair exhibited a cosmetically acceptable wave, with no apparent signs of damage. (In the opinion of the recipient, her hair was marginally lightened to the same extent she has noticed with previous perms.) This wave has persisted for 13 weeks. At 7 weeks post-treatment, the hair was cut by a beautician, who stated the wave was "strong" and the hair exhibited no apparent signs of damage or dryness.

7.3. HARD-TO-PERM CAUCASIAN HAIR

The recipient, a Caucasian female with a history of experiencing either severe hair damage from perms or perms that did not last beyond a few weeks, was given a wave with the following composition for the reduction stage:

| Active Ingredient[a] | Concentration (Molarity) |
|---|---|
| Glycerol Monothioglycolate | 0.85 |
| Potassium Iodide | 0.3 |
| Ammonia[b] | |

[a] Ingredients mixed just prior to use.
[b] Used to adjust pH to 6.8.

It should be noted that commercially available perms using glycerol monothioglycolate range from 1.1–1.2 M in concentration.

The hair was processed for 23 minutes under a salon hair dryer at the "Normal" setting. After rinsing for 5 minutes, it was neutralized with sodium bromate (10%) with 5% urea added as a flame retardant. There was no noticeable iodine formation.

The treated hair exhibited a cosmetically acceptable wave with small, springy curls and, according to the recipient and the beautician, the hair had a healthy, undamaged appearance and feel.

8. EXAMPLE: STRAIGHTENING HAIR

A composition for the reduction stage was prepared as a lotion as follows:

| Active Ingredient | Concentration (Molarity) |
|---|---|
| Sodium bisulfite | 1.0 |
| Potassium Iodide | 0.3 |
| Ammonia (aqueous)[a] | |

[a] Used to adjust pH to 7.0

Samples of human hair (DeMeo Brothers, New York, N.Y.) that had previously been treated with a permanent wave process were wet with water, shampooed and wrapped around a large-bore cylinder. The lotion was applied using a heat-activated method. The hair was maintained at about body temperature for 20 minutes. Subsequently, the hair was thoroughly rinsed with water and treated with a neutralizing composition of 10% cosmetic grade sodium bromate at pH 7.5.

Control samples of hair were treated using an identical process, except that potassium iodide was not added to the reducing composition.

The hair samples treated with the composition containing potassium iodide achieved a cosmetically straight configuration. Control samples, however, still retained a portion of the curled or waved configuration post-treatment.

Having described the invention with particular reference to certain embodiments thereof, it will be obvious to those skilled in the art to which the invention pertains after understanding the invention, that various changes and modifications may be made therein without departing from the spirit and scope of the invention as defined by the claims appended hereto.

What is claimed is:

1. A reducing composition for reducing disulfide bonds of keratin, comprising an aqueous solution of a water soluble iodide salt and a water soluble keratin reducing thioglycolate salt, in which the concentration of the iodide salt is from about 0.05 to about 1 molar and the concentration of the thioglycolate salt is from about 0.4 to about 1.2 molar.

2. The reducing composition according to claim 1, in which the concentration of iodide salt is from about 0.15 to about 1 molar.

3. The reducing composition according to claim 1, in which the concentration of the keratin reducing thioglycolate salt is from about 0.5 to about 1 molar.

4. The reducing composition according to claim 1, in which the keratin reducing thioglycolate salt is ammonium thioglycolate.

5. The reducing composition according to claim 1, in which the keratin reducing thioglycolate salt is monoethanolammonium thioglycolate.

6. A reducing composition for reducing disulfide bonds of keratin, comprising an aqueous solution of a water soluble iodide salt and a water soluble, consumable keratin reducing agent selected from the group consisting of salts of sulfites, bisulfites, hydrobisulfites, metabisulfites and sulfoxylates, in which the concentration of the iodide salt is from about 0.15 to about 1 molar and the concentration of the consumable reducing agent is from about 0.3 to about 2 molar.

7. The reducing composition according to claim 6, in which the concentration of the consumable keratin reducing agent is from about 0.7 to about 2 molar.

8. The reducing composition according to claim 6, in which the consumable keratin reducing agent is a sulfite salt.

9. The reducing composition according to claim 6, in which the consumable keratin reducing agent is a bisulfite salt.

10. A process for setting hair or fur, comprising:
   (a) applying to hair or fur a reducing composition according to claim 1;
   (b) allowing the hair or fur to stand in a desired configuration;
   (c) applying to the hair or fur a sufficient amount of an aqueous neutralizing composition to provide permanent waving or straightening of the hair or fur; and
   (d) washing and drying the hair or fur.

11. A process for setting hair or fur, comprising:
   (a) applying to hair or fur a reducing composition according to claim 6;
   (b) allowing the hair or fur to stand in a desired configuration;
   (c) applying to the hair or fur a sufficient amount of an aqueous neutralizing composition to provide permanent waving or straightening of the hair or fur; and
   (d) washing and drying the hair or fur.

12. A reducing composition for reducing disulfide bonds of keratin, comprising an aqueous solution of a water soluble iodide salt and glycerol monothioglycolate, in which the concentration of the iodide salt is from about 0.05 to about 1 molar and the concentration of the glycerol monothioglycolate is from about 0.6 about 1.5 molar.

13. The reducing composition according to claim 12, in which the concentration of the iodide salt is from about 0.15 to about 1 molar.

14. A process for setting hair or fur, comprising:
   (a) applying to hair or fur a reducing composition according to claim 12,
   (b) allowing the hair or fur to stand in a desired configuration;
   (c) applying to the hair or fur a sufficient amount of an aqueous neutralizing composition to provide permanent waving or straightening of the hair or fur; and (d) washing and drying the hair or fur.

15. A process for setting hair or fur, comprising:
(a) applying to hair or fur a reducing composition comprising an aqueous solution of a water soluble iodide salt and a water soluble, consumable keratin reducing agent selected from the group consisting of sulfites, bifulites, hydrobisulfites, metabisulfites and sulfoxylates, in which the concentration of the iodide salt is from about 0.05 to about 1 molar and the concentration of the consumable keratin reducing agent is from about 0.3 to about 2 molar;
(b) allowing the hair or fur to stand in a desired configuration;
(c) applying to the hair or fur a sufficient amount of an aqueous neutralizing composition to provide permanent waving or straightening of the hair or fur; and
(d) washing and drying the hair or fur.

16. The process according to claim 10, 11, 14 or 15, in which the neutralizing composition comprises sodium bromate.

17. The process according to claim 10, 11, 14 or 15, in which the neutralizing composition comprises potassium antimony (V) tartrate.

18. The process according to claim 10, 11, 14 or 15, in which the neutralizing composition comprises hydrogen peroxide with a sufficient amount of a protective reducing agent to reduce any iodine to iodide.

19. The process according to claim 18, in which the protective reducing agent is ascorbic acid.

20. The process according to claim 18, in which the protective reducing agent is carbazide.

* * * * *